US011306273B2

(12) United States Patent
Denutte et al.

(10) Patent No.: US 11,306,273 B2
(45) Date of Patent: *Apr. 19, 2022

(54) CONSUMER PRODUCTS AND DELIVERY SYSTEMS UTILIZING ORGANOLEPTIC COMPOUNDS

(71) Applicant: The Procter & Gamble Company, Cincinnati, OH (US)

(72) Inventors: Hugo Robert Germain Denutte, Hofstade (BE); Johan Smets, Lubbeek (BE); Philip John Porter, Mason, OH (US); Freek Annie Camiel Vrielynck, Beernem (BE); Koen Van Aken, Kuurne (BE); Bart Antoon Judith Ruttens, Wetteren (BE); Anubhav P. S. Narula, Hazlet, NJ (US); Richard A. Weiss, Livingston, NJ (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/659,605

(22) Filed: Oct. 22, 2019

(65) Prior Publication Data

US 2020/0131450 A1 Apr. 30, 2020

Related U.S. Application Data

(60) Provisional application No. 62/749,693, filed on Oct. 24, 2018.

(51) Int. Cl.

| | |
|---|---|
| ***A61K 8/18*** | (2006.01) |
| ***A61Q 13/00*** | (2006.01) |
| ***A61K 8/00*** | (2006.01) |
| ***C11B 9/00*** | (2006.01) |
| ***C11D 3/50*** | (2006.01) |

(52) U.S. Cl.

CPC ............ *C11B 9/0034* (2013.01); *C11D 3/507* (2013.01)

(58) Field of Classification Search

CPC .... C11B 9/0034; C07C 49/21; C07C 2601/16

USPC ........................................................ 512/22, 8, 1

See application file for complete search history.

(56) References Cited

U.S. PATENT DOCUMENTS

| | | | | |
|---|---|---|---|---|
| 6,844,302 | B1 | 1/2005 | Boden | |
| 9,328,319 | B2 | 5/2016 | Ravidat | |
| 2012/0329696 | A1 * | 12/2012 | Denutte | C11D 3/3481 510/103 |
| 2020/0131451 | A1 * | 4/2020 | Narula | C11B 9/0034 |

FOREIGN PATENT DOCUMENTS

| | | | |
|---|---|---|---|
| CN | 103429218 | A | 12/2013 |
| CN | 104066828 | A | 9/2014 |
| JP | S5058246 | A | 5/1975 |

OTHER PUBLICATIONS

Makiko et al., JP 2013199450 Machine Translation, Oct. 3, 2013 (Year: 2013).*

Case 15380M Search Report; PCT/US2019/057350; Dated Jan. 15, 2020; 13 Pages.

* cited by examiner

*Primary Examiner* — Jessica Whiteley

(74) *Attorney, Agent, or Firm* — Abbey A. Lopez

(57) ABSTRACT

The present application relates to perfume delivery systems and consumer products comprising a novel organoleptic compound and or perfume delivery systems having the novel organoleptic compound, as well as methods for using such perfume delivery systems and consumer products.

18 Claims, No Drawings

CONSUMER PRODUCTS AND DELIVERY SYSTEMS UTILIZING ORGANOLEPTIC COMPOUNDS

FIELD

The present application relates to consumer products and perfume delivery systems using organoleptic compounds, as well as processes for making and using such consumer products and perfume delivery systems.

JOINT RESEARCH AGREEMENT

The inventions described and claimed herein were made pursuant to a Joint Research Agreement between The Procter & Gamble Company and International Flavors & Fragrances, Inc., New York, N.Y.

BACKGROUND

Consumer products may comprise one or more perfumes and/or perfume delivery systems that can mask an undesirable odor and/or provide a desired scent to a product or an area that is contacted with such a product. While current perfumes and perfume delivery systems provide desirable fragrances, consumers continue to seek products that have scents that may be longer lasting and that are tailored to their individual desires (see for example USPA 2007/0275866 A1 and USPA 2008/0305977 A1)—unfortunately the pool of perfume raw materials and perfume delivery systems that is available is still too limited to completely meet the perfume community's needs. Thus, perfumers need an ever-larger pool of perfume raw materials and perfume delivery systems.

SUMMARY

Subcombinations:

A. A consumer product comprising an organoleptic compound of formula:

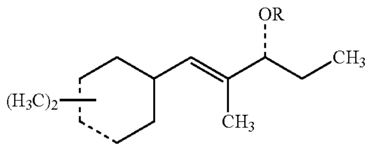

wherein R represents H; one of the dashed lines in the ring represents a carbon-carbon single bond with the other representing a carbon-carbon double bond; and the dashed line in the chain represents a carbon-carbon single bond or a carbon-carbon double bond, with the proviso that when the dashed line in the chain represents a carbon-carbon double bond, R is absent.

B. The consumer product according to Paragraph A, wherein the organoleptic compound is selected from the group consisting of:

(E)-1-((1R,6R)-4,6-dimethylcyclohex-3-en-1-yl)-2-methylpent-1-en-3-one;

(E)-1-((1S,6S)-3,6-dimethylcyclohex-3-en-1-yl)-2-methylpent-1-en-3-one;

(E)-1-((1R,6S)-4,6-dimethylcyclohex-3-en-1-yl)-2-methylpent-1-en-3-one;

(E)-1-((1S,6R)-3,6-dimethylcyclohex-3-en-1-yl)-2-methylpent-1-en-3-one;

(E)-1-((1R,6R)-4,6-dimethylcyclohex-3-en-1-yl)-2-methylpent-1-en-3-ol;

(E)-1-((1S,6S)-3,6-dimethylcyclohex-3-en-1-yl)-2-methylpent-1-en-3-ol;

(E)-1-((1R,6S)-4,6-dimethylcyclohex-3-en-1-yl)-2-methylpent-1-en-3-ol;

(E)-1-((1S,6R)-3,6-dimethylcyclohex-3-en-1-yl)-2-methylpent-1-en-3-ol; and a mixture thereof.

C. The consumer product according to Paragraph B, wherein the organoleptic compound is the mixture of (E)-1-((1R,6R)-4,6-dimethylcyclohex-3-en-1-yl)-2-methylpent-1-en-3-one, (E)-1-((1S,6S)-3,6-dimethylcyclohex-3-en-1-yl)-2-methylpent-1-en-3-one, (E)-1-((1R,6S)-4,6-dimethylcyclohex-3-en-1-yl)-2-methylpent-1-en-3-one and (E)-1-((1S,6R)-3,6-dimethylcyclohex-3-en-1-yl)-2-methylpent-1-en-3-one.

D. The consumer product according to any of Paragraphs A through C, wherein the consumer product is a cleaning and/or treatment composition, said composition comprising, based on total composition weight, from about 0.0001% to about 25% of the organoleptic compound.

E. The consumer product according to any of Paragraphs A through D, wherein the consumer product is a fabric and/or hard surface cleaning and/or treatment composition, said composition comprising, based on total composition weight, from about 0.00001% to about 25% of the organoleptic compound.

F. The consumer product according to any of Paragraphs A through E, wherein the consumer product is a detergent, said detergent comprising, based on total detergent weight, from about 0.00001% to about 25% of the organoleptic compound.

G. The consumer product according to any of Paragraphs A through F, wherein the consumer product is a highly compacted consumer product, said highly compacted consumer product comprising, based on total highly compacted consumer product weight, from about 0.00001% to about 25% of the organoleptic compound.

H. A method of treating an area with the consumer product of any of Paragraphs A through I. A perfume delivery system comprising an organoleptic compound of formula:

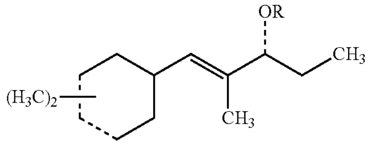

wherein R represents H; one of the dashed lines in the ring represents a carbon-carbon single bond with the other representing a carbon-carbon double bond; and the dashed line in the chain represents a carbon-carbon single bond or a carbon-carbon double bond, with the proviso that when the dashed line in the chain represents a carbon-carbon double bond, R is absent.

J. The perfume delivery system of Paragraph I, wherein the organoleptic compound is selected from the group consisting of:

(E)-1-((1R,6R)-4,6-dimethylcyclohex-3-en-1-yl)-2-methylpent-1-en-3-one;

(E)-1-((1S,6S)-3,6-dimethylcyclohex-3-en-1-yl)-2-methylpent-1-en-3-one;

(E)-1-((1R,6S)-4,6-dimethylcyclohex-3-en-1-yl)-2-methylpent-1-en-3-one;
(E)-1-((1S,6R)-3,6-dimethylcyclohex-3-en-1-yl)-2-methylpent-1-en-3-one;
(E)-1-((1R,6R)-4,6-dimethylcyclohex-3-en-1-yl)-2-methylpent-1-en-3-ol;
(E)-1-((1S,6S)-3,6-dimethylcyclohex-3-en-1-yl)-2-methylpent-1-en-3-ol;
(E)-1-((1R,6S)-4,6-dimethylcyclohex-3-en-1-yl)-2-methylpent-1-en-3-ol;
(E)-1-((1S,6R)-3,6-dimethylcyclohex-3-en-1-yl)-2-methylpent-1-en-3-ol; and
a mixture thereof, wherein said perfume delivery system is selected from a polymer assisted delivery system; a molecule-assisted delivery system; a fiber-assisted delivery system; an amine assisted delivery system; a cyclodextrin delivery system; a starch encapsulated accord; an inorganic carrier delivery system; or a pro-perfume.

K. The perfume delivery system of Paragraph J, wherein the organoleptic compound is the mixture of (E)-1-((1R,6R)-4,6-dimethylcyclohex-3-en-1-yl)-2-methylpent-1-en-3-one, (E)-1-((1S,6S)-3,6-dimethylcyclohex-3-en-1-yl)-2-methylpent-1-en-3-one, (E)-1-((1R,6S)-4,6-dimethylcyclohex-3-en-1-yl)-2-methylpent-1-en-3-one and (E)-1-((1S,6R)-3,6-dimethylcyclohex-3-en-1-yl)-2-methylpent-1-en-3-one.

L. The perfume delivery system according to any of Paragraphs I through K further comprising, based on total perfume delivery system weight, from about 0.1% to about 99% of the organoleptic compound.

M. A perfume delivery system according to any of Paragraphs I through L, wherein the perfume delivery system is a capsule.

N. A perfume delivery system according to any of Paragraphs I through M, wherein perfume delivery system is a starch encapsulated accord.

O. A method of treating an area with a consumer product comprising the perfume delivery system of any of Paragraphs I through N.

DETAILED DESCRIPTION

The following definitions may be useful for understanding the invention of the present disclosure.

As used herein "consumer product" means baby care, beauty care, fabric and home care, family care, feminine care or health care products generally intended to be used or consumed in the form in which it is sold.

"Baby care" includes such products include but are not limited to products and/or methods relating to disposable absorbent and/or non-absorbent articles including adult incontinence garments, bibs, diapers, training pants, infant and toddler care wipes; and personal care products, including hand soaps, shampoos, lotions, oral care implements, and clothing.

"Beauty care" includes products for and/or methods relating to treating hair (human, dog, and/or cat), including, bleaching, coloring, dyeing, conditioning, growing, removing, retarding growth, shampooing, styling; deodorants and antiperspirants; personal cleansing; color cosmetics; products, and/or methods relating to treating skin (human, dog, and/or cat), including application of creams, lotions, and other topically applied products for consumer use; and products and/or methods relating to orally administered materials for enhancing the appearance of hair, skin, and/or nails (human, dog, and/or cat); and shaving.

"Fabric and home care" includes products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer and or institutional use.

"Family care" includes products such as wet or dry bath tissue, facial tissue, disposable handkerchiefs, disposable towels, and/or wipes, as well as methods and equipment for making such products.

"Feminine care" includes products and/or methods relating to catamenial pads, incontinence pads, interlabial pads, panty liners, pessaries, sanitary napkins, tampons and tampon applicators, and/or wipes.

"Health care" includes products and/or methods relating to: oral care including any composition for use with any soft and/or hard tissue of the oral cavity or conditions associated therewith (e.g., anti-caries compositions, anti-microbial compositions, anti-plaque chewing gum compositions, breath compositions, confectionaries, dentifrices, denture compositions, lozenges, rinses, and tooth whitening compositions), cleaning devices, floss and flossing devices, and toothbrushes; over-the-counter health care including cough and cold remedies and treatments for other respiratory conditions, pain relievers whether topical, oral, or otherwise, gastrointestinal remedies including any composition suitable for the alleviation of gastrointestinal conditions such as heartburn, upset stomach, diarrhea, and irritable bowel syndrome, and nutrient supplementation such as calcium or fiber supplementation; pharmaceutical care including pharmacologically active molecular and/or biological entities, their use in the treatment and/or prevention of diseases and/or alleviation of symptoms in humans and/or animals, and formulations, regimens, kits and/or routes of delivering such entities to subjects in need of treatment and/or prevention and/or alleviation, discovery tools including screening methods, assays, and receptors, and their use in discovering new pharmacologically active molecular and/or biological entities; pet health and nutrition including pet foods, treats, other orally deliverable products, regardless of distribution channel (including veterinary and over-the-counter), as well as topical products such as grooming aids, training aids, devices, toys, and diagnostic techniques; and waters including purified, flavored, or other treated waters.

As used herein, the term "cleaning and/or treatment composition" is a subset of consumer products that includes, unless otherwise indicated, beauty care, fabric & home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products which were applicable may be in standard, concentrated or even highly concentrated form even to the extent that such products may in certain aspect be non-aqueous. Fabric and/or hard surface cleaning and/or treatment compositions may be configured to be sprayable, pourable, dosable, and the like.

As used herein, articles such as "a" and "an" when used in a claim, are understood to mean one or more of what is claimed or described.

As used herein, the terms "include", "includes" and "including" are meant to be non-limiting.

As used herein, the term "solid" includes granular, powder, bar and tablet product forms.

As used herein, the term "fluid" includes liquid, gel, paste and gas product forms.

As used herein, the term "area" is used to reference the location or space to be treated or cleaned with a consumer product. An area may be a substrate, paper product, fabric, garment, hard surface, hair, skin, air, and the like.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Organoleptic Compounds

Consumer products and/or delivery systems of the present invention may benefit from the introduction of novel organoleptic compounds to enhance, improve, and/or modify the fragrance thereof.

More specifically, the present invention relates to consumer products and delivery systems utilizing an organoleptic compound, (dimethylcyclohex-3-en-1-yl)-2-methylpent-1-en-3-ones (ols), represented by Formula I that set forth below:

Formula I

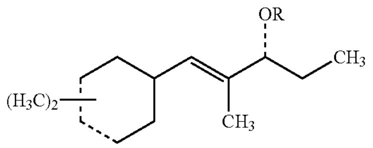

wherein R represents H and one of the dashed lines in the ring represents a carbon-carbon single bond with the other representing a carbon-carbon double bond, and the dashed line in the chain represents a carbon-carbon single bond or a carbon-carbon double bond; with the proviso that when the dashed line in the chain represents a carbon-carbon double bond, the R group is absent The (dimethylcyclohex-3-en-1-yl)-2-methylpent-1-en-3-one (ol) compounds represented by Formula I of the present invention are illustrated by following examples.

(E)-1-((1R,6R)-4,6-dimethylcyclohex-3-en-1-yl)-2-methylpent-1-en-3-one

Structure 1

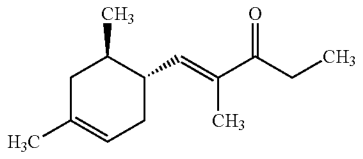

(E)-1-((1S,6S)-3,6-dimethylcyclohex-3-en-1-yl)-2-methylpent-1-en-3-one

Structure 2

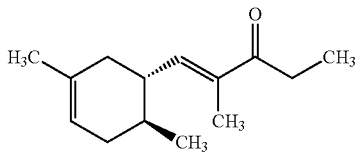

(E)-1-((1R,6S)-4,6-dimethylcyclohex-3-en-1-yl)-2-methylpent-1-en-3-one

Structure 3

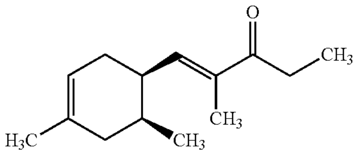

(E)-1-((1S,6R)-3,6-dimethylcyclohex-3-en-1-yl)-2-methylpent-1-en-3-one

Structure 4

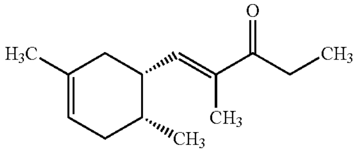

(E)-1-((1R,6R)-4,6-dimethylcyclohex-3-en-1-yl)-2-methylpent-1-en-3-ol

Structure 5

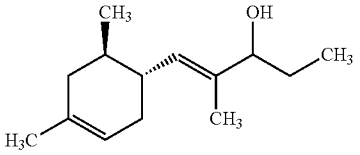

(E)-1-((1S,6S)-3,6-dimethylcyclohex-3-en-1-yl)-2-methylpent-1-en-3-ol

Structure 6

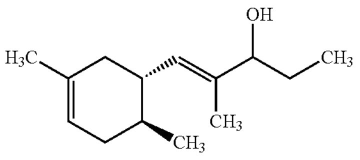

(E)-1-((1R,6S)-4,6-dimethylcyclohex-3-en-1-yl)-2-methylpent-1-en-3-ol

Structure 7

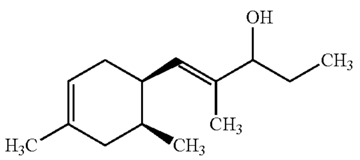

(E)-1-((1S,6R)-3,6-dimethylcyclohex-3-en-1-yl)-2-methylpent-1-en-3-ol

Structure 8

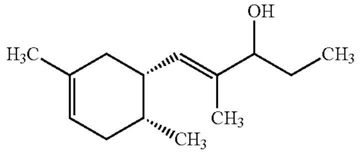

Those with skill in the art will recognize that the compounds of the present invention may have a number of isomers such as positional isomers depending on the available starting materials. It is intended herein that the compounds described herein include isomeric mixtures as well as single isomers that may be separated using techniques known to those having skill in the art. Suitable techniques include chromatography such as high-performance liquid chromatography, referred to as HPLC, and particularly silica gel chromatography and gas chromatography trapping known as GC trapping. Yet, commercial products are mostly offered as isomeric mixtures. The term "an organoleptic compound" is understood to mean one or more of the (dimethylcyclohex-3-en-1-yl)-2-methylpent-1-en-3-ones (ols) represented by Structures 1-8 as described herein. The preparation of the organoleptic compounds of the present invention is detailed in the Examples. Structures 5-8 can be readily prepared from corresponding sStructures 1-4 via hydrogenation using Lithium aluminum hydride ($LiAlH_4$). Materials were purchased from Aldrich Chemical Company unless noted otherwise.

The organoleptic compounds of the present invention, for example, possess strong and complex fresh, crispy, slight green, resinous, coniferous, floral, ionone-like, ambery, woody and diffusive notes.

In these preparations, the organoleptic compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The organoleptic compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl)cyclohexene-1-carboxaldehyde (Lyral), 3-methyl-4-(2,6,6-trimethyl-2-cyclohexen-1-yl)-3-buten-2-one (Methyl Ionone γ), 6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolyl ethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff/Isovertoliff), and (3Z)-1-[(2-methyl-2-propenyl)oxy]-3-hexene (Vivaldie).

Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The term "alkyl" means a linear or branched saturated monovalent hydrocarbon, e.g., methyl, ethyl, propyl, 2-propyl, butyl (including all isomeric forms), pentyl (including all isomeric forms), hexyl (including all isomeric forms), and the like. The term "alkenyl" means a linear or branched unsaturated, aliphatic hydrocarbon containing at least one carbon-carbon double bond. The term "alkylene" refers to bivalent alkyl. Examples include —CH2-, —CH2CH2-, —CH2CH2CH2-, —CH2(CH3)CH2-, —CH2CH2CH2CH2-, and the like.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Consumer Products

The use of the organoleptic compounds of the present invention is widely applicable in current consumer products, including personal care products such as soaps, shower gels, and hair care products, fabric care products, air fresheners, and cosmetic preparations. The present invention can also be used with cleaning agents, such as, but not limited to detergents, dishwashing materials, scrubbing compositions, window cleaners and the like.

The organoleptic compounds of Formula I and stereoisomers thereof are suitable for use in consumer products at levels, based on total consumer product weight, of from about 0.0001% to about 25%, from about 0.0005% to about 10%, from about 0.001% to about 5%, from about 0.005% to about 2.5%, or even from 0.01% to about 1%. Such organoleptic compounds of Formula I and stereoisomers thereof may be used in various combinations in the aforementioned consumer products. A consumer product may comprise one or more organoleptic compounds of Formula I and stereoisomers thereof selected from Structures 1-8 and stereoisomers thereof.

The organoleptic compounds of Formula I and stereoisomers thereof are suitable for use in cleaning and/or treatment compositions at levels, based on total cleaning and treatment products weight of from about 0.0001% to about 25%, from about 0.0005% to about 10%, from about 0.001% to about 5%, from about 0.005% to about 2.5%, or even from 0.01% to about 1%. Such organoleptic compounds of Formula I and stereoisomers thereof may be used in various combinations in the aforementioned cleaning and/treatment compositions. A cleaning and/or treatment composition may comprise one or more organoleptic compounds of Formula I and stereoisomers thereof selected from Structures 1-8 and stereoisomers thereof.

The organoleptic compounds of Formula I and stereoisomers thereof are suitable for use in fabric and/or hard surface cleaning and/or treatment compositions at levels, based on total fabric and/or hard surface cleaning and/or treatment composition weight of from about 0.00001% to about 25%, from 0.00005% to about 10%, from 0.0001% to about 5%, from 0.0005% to about 1.0%, or even from 0.001% to about 0.5%. Such PRMs and stereoisomers thereof may be used in various combinations in the aforementioned fabric and/or hard surface cleaning and/or treatment compositions. A fabric and/or hard surface cleaning and/or treatment composition may comprise one or more organoleptic compounds of Formula I and stereoisomers thereof selected from Structures 1-8 and stereoisomers thereof.

A detergent that may comprise the same level of the organoleptic compounds of Formula I as disclosed for the aforementioned fabric and hard surface cleaning and/or treatment compositions is disclosed. A detergent may comprise one or more organoleptic compounds of Formula I and stereoisomers thereof selected from Structures 1-8 and stereoisomers thereof.

The organoleptic compounds of Formula I and stereoisomers thereof are suitable for use in highly compacted consumer products, including highly compacted fabric and hard-surface cleaning and/or treatment compositions. For example, the organoleptic compounds of Formula I and stereoisomers thereof may be employed in solid or fluid highly compacted detergents at levels of from about 0.00001% to about 25%, from 0.00005% to about 10%, from 0.0001% to about 5%, from 0.0005% to about 1.0%, or even from 0.001% to about 0.5%, based on total composition weight. Such organoleptic compounds of Formula I and stereoisomers thereof may be used in various combinations in the aforementioned highly compacted detergent compositions. Such highly compact detergents typically comprise a higher than normal percentage of active ingredients. A highly compacted detergent may comprise one or more organoleptic compounds of Formula I and stereoisomers thereof. More specifically, a highly compacted detergent may comprise one or more organoleptic compounds of Formula I and stereoisomers thereof selected from Structures 1-8 and stereoisomers thereof.

In addition, the organoleptic compounds of the present invention are also surprisingly found to provide superior ingredient performance and possess unexpected advantages in malodor counteracting applications such as body perspiration, environmental odor such as mold and mildew, bathroom, and etc. The organoleptic compounds of the present invention substantially eliminate the perception of malodors and/or prevent the formation of such malodors, thus, can be utilized with a vast number of functional products.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the organoleptic compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the organoleptic compounds of the present invention may be present in an amount ranging from about 0.1 to 10 mg per cubic meter of air.

Perfume Delivery Systems

The organoleptic compounds of the present invention may further be incorporated into a perfume delivery system. Suitable perfume delivery systems, methods of making perfume delivery systems and the uses of perfume delivery systems are disclosed in USPA 2007/0275866 A1. The organoleptic compounds of Formula I and stereoisomers thereof are suitable for use in perfume delivery systems at levels, based on total perfume delivery system weight, of from about 1% to about 99%, from about 2.5% to about 75%, from 5% about to about 60%, from about 5% to about 50%, from about 5% to about 25%. A perfume delivery system may comprise one or more compounds of Formula I, and stereoisomers thereof, selected from Structures 1-8 and mixtures thereof.

The perfume delivery technologies (a.k.a., perfume delivery systems) that are disclosed in the present specification may be used in any combination in any type of consumer product, cleaning and/or treatment composition, fabric and hard-surface cleaning and/or treatment composition, detergent, and/or highly compact detergent. The perfume delivery systems disclosed herein are suitable for use in consumer products, cleaning and treatment compositions, fabric and hard surface cleaning and/or treatment compositions, detergents, and highly compacted consumer products, including highly compacted fabric and hard surface cleaning and/or treatment compositions (e.g., solid or fluid highly compacted detergents) at levels, based on total consumer product weight, from about 0.001% to about 20%, from about 0.01% to about 10%, from about 0.05% to about 5%, from about 0.1% to about 0.5%.

Such perfume delivery systems include:

I. Polymer Assisted Delivery (PAD): This perfume delivery technology uses polymeric materials to deliver the organoleptic compounds of Formula I, stereoisomers thereof, and additional perfume materials. Examples of PAD include employment of classical coacervation, water soluble or partly soluble to insoluble charged or neutral polymers, liquid crystals, hot melts, hydrogels, perfumed plastics, capsules, nano- and micro-latexes, polymeric film formers, and polymeric absorbents, etc.

PAD systems include, but are not limited to:

a.) Matrix Systems: the organoleptic compounds of Formula I, stereoisomers thereof, and additional perfume materials are dissolved or dispersed in a polymer matrix or particle. The organoleptic compounds of Formula I, stereoisomers thereof, and additional perfume materials may be 1) dispersed into the polymer prior to formulating into the product or 2) added separately from the polymer during or after formulation of the product. Suitable organic latex particles include a wide range of materials including, but not limited to, polyacetal, polyacrylate, polyamide, polybutadiene, polychloroprene, polyethylene, polycyclohexylene polycarbonate, polyhydroxyalkanoate, polyketone, polyester, polyetherimide, polyethersulfone, polyethylenechlorinates, polyimide, polyisoprene, polylactic acid, polyphenyl ene, polyphenylene, polypropylene, polystyrene, polysulfone, polyvinyl acetate, polyvinyl chloride, as well as polymers or copolymers based on amine, acrylonitrile-butadiene, cellulose acetate, ethylene-vinyl acetate, ethylene vinyl alcohol, styrene-butadiene, vinyl acetate-ethylene, and mixtures thereof. All such matrix systems may include, for example, polysaccharides and nanolatexes that may be combined with other perfume delivery technologies, including other PAD systems such as PAD reservoir systems in the form of a perfume capsule (PC). Silicone-assisted delivery (SAD) may also be used. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP).

b.) Reservoir Systems: Reservoir systems are also known as core-shell systems (e.g., perfume capsules). In such a system, the benefit agent is surrounded by a benefit agent release controlling membrane, which may serve as a protective shell. Capsules may comprise one or more of organoleptic compounds of Formula I and stereoisomers thereof, selected from Structures 1-8 and mixtures thereof.

Suitable shell materials include reaction products of one or more amines with one or more aldehydes, such as urea cross-linked with formaldehyde or gluteraldehyde, melamine cross-linked with formaldehyde, gelatin-polyphosphate coacervates optionally cross-linked with gluteraldehyde, gelatin-gum arabic coacervates, cross-linked silicone fluids, polyamine reacted with polyisocyanates, polyamines reacted with epoxides, polyvinyl alcohol cross linked with gluteraldehyde, polydivinyl chloride, polyesters, polyamides, polyacrylates and mixtures thereof. The polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof.

Core materials include the organoleptic compounds of Formula I and stereoisomers thereof, perfume compositions, perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers and anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, and natural actives such as aloe vera, vitamin E, shea butter, cocoa butter, and the like, brighteners, antibacterial actives, antiperspirant actives, cationic polymers, dyes and mixtures thereof. Suitable perfume compositions may comprise enduring perfumes, such as perfume raw materials that have a log P greater than about 2.5 and a boiling point greater than about 250° C. Further, suitable perfume compositions may comprise blooming perfumes that comprise perfume raw materials that have a log P of greater than about 3 and a boiling point of less than about 260° C.

Suitable core materials can be stabilized and/or emulsified in solvent systems with organic or inorganic materials (organic materials can be polymers of anionic nature, nonionic nature or cationic nature, like polyacrylates and polyvinyl alcohol). Suitable processes to make core-shell systems include coating, extrusion, spray drying, interfacial polymerization, polycondensation, simple coacervation, complex coacervation, free radical polymerization, in situ emulsion polymerization, matrix polymerization and combinations thereof.

Suitable characteristics for the core-shell systems include:

a) a shell thickness of from about 20 nm to about 500 nm, from about 40 nm to about 250 nm, or from about 60 nm to about 150 nm;

b) a shell core ratio of from about 5:95 to about 50:50, from about 10:90 to about 30:70, or from about 10:90 to about 15:85;

c) a fracture strength of from about 0.1 MPa to about 16 MPa, from about 0.5 MPa to about 8 MPa, or even from about 1 MPa to about 3 MPa; and d) an average particle size of from about 1 micron to about 100 microns, from about 5 microns to about 80 microns, or even from about 15 microns to about 50 microns.

Suitable deposition and/or retention enhancing coatings may be applied to the core-shell systems and include nonionic polymers, anionic polymers, cationic polymers such as polysaccharides including, but not limited to, cationically modified starch, cationically modified guar, chitosan, polysiloxanes, poly diallyl dimethyl ammonium halides, copolymers of poly diallyl dimethyl ammonium chloride and vinyl pyrrolidone, acrylamides, imidazoles, imidazolinium halides, imidazolium halides, poly vinyl amine, copolymers of poly vinyl amine and N-vinyl formamide and mixtures thereof. Suitable coatings may be selected from the group consisting of polyvinylformaldehyde, partially hydroxylated polyvinylformaldehyde, polyvinylamine, polyethyleneimine, ethoxylated polyethyleneimine, polyvinylalcohol, polyacrylates and combinations thereof.

Suitable methods of physically reducing and/or removing any residual type materials from the core-shell making process may be employed, such as centrifugation. Suitable methods of chemically reducing any residual type materials may also be employed, such as the employment of scavengers, for example formaldehyde scavengers including sodium bisulfite, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly(vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly (l-lysine), chitosan, hexane diol, ethylenediamine-N,N'-bisacetoacetamide, N-(2-ethylhexyl)acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or mixtures thereof.

Polyacrylate Capsules

Polyacrylate capsules comprise a core and an outer shell encapsulating said core wherein said shell comprises polyacrylate polymer. The shell may include from about 50% to about 100%, or from about 70% to about 100%, or from about 80% to about 100% of a polyacrylate polymer. The polyacrylate may include a polyacrylate cross linked polymer.

Polyacrylate capsules comprise an outer shell defining a core in which a benefit agent is held until rupture of the shell.

The shell material may include a material selected from the group consisting of a polyacrylate, a polyethylene glycol acrylate, a polyurethane acrylate, an epoxy acrylate, a polymethacrylate, a polyethylene glycol methacrylate, a polyurethane methacrylate, an epoxy methacrylate, and mixtures thereof.

The shell material of the capsules may include a polymer derived from a material that comprises one or more multi-functional acrylate moieties. The multifunctional acrylate moiety may be selected from the group consisting of tri-functional acrylate, tetra-functional acrylate, penta-functional acrylate, hexa-functional acrylate, hepta-functional acrylate and mixtures thereof. The multifunctional acrylate moiety is preferably hexa-functional acrylate. The shell material may include a polyacrylate that comprises a moiety selected from the group consisting of an acrylate moiety, methacrylate moiety, amine acrylate moiety, amine methacrylate moiety, a carboxylic acid acrylate moiety, carboxylic acid methacrylate moiety and combinations thereof, preferably an amine methacrylate or carboxylic acid acrylate moiety.

The shell material may include a material that comprises one or more multifunctional acrylate and/or methacrylate moieties. The ratio of material that comprises one or more multifunctional acrylate moieties to material that comprises one or more methacrylate moieties may be from about 999:1 to about 6:4, preferably from about 99:1 to about 8:1, more preferably from about 99:1 to about 8.5:1.

The core/shell capsule may comprise an emulsifier, wherein the emulsifier is preferably selected from anionic emulsifiers, nonionic emulsifiers, cationic emulsifiers or mixtures thereof, preferably nonionic emulsifiers.

The core/shell capsule may comprise from 0.01% to 20%, more preferably from 0.05% to 10%, even more preferably from 0.1% to 5%, most preferably from 0.1% to 2% by weight of the core/shell capsule of polyvinyl alcohol. Preferably, the polyvinyl alcohol has at least one the following properties, or a mixture thereof:

(i) a hydrolysis degree from 55% to 99%, preferably from 75% to 98%, more preferably from 80% to 96%, more preferably 82% to 96%, most preferably from 86% to 94%;

(ii) a viscosity of from 2 mPa·s to 150 mPa·s, preferably from 3 mPa·s to 70 mPa·s, more preferably from 4 mPa·s to 60 mPa·s, even more preferably from 5 mPa·s to 55 mPa·s in 4% water solution at 20° C.;

(iii) a degree of polymerization of from 1,500 to 2,500;

(iv) number average molecular weight of from 65,000 Da to 110,000 Da.

Suitable polyvinylalcohol materials may be selected from Selvol 540 PVA (Sekisui Specialty Chemicals, Dallas, Tex.), Mowiol 18-88=Poval 18-88, Mowiol 3-83, Mowiol 4-98=Poval 4-98 (Kuraray), Poval KL-506=Poval 6-77 KL (Kuraray), Poval R-1130=Poval 25-98 R (Kuraray), Gohsenx K-434 (Nippon Gohsei).

II. Molecule-Assisted Delivery (MAD): Non-polymer materials or molecules may also serve to improve the delivery of the organoleptic compounds of Formula I, stereoisomers thereof, and additional perfume materials as these materials may non-covalently interact with organic materials, resulting in altered deposition and/or release. Non-limiting examples of such organic materials include, but are not limited to, hydrophobic materials such as organic oils, waxes, mineral oils, petrolatum, fatty acids or esters, sugars, surfactants, liposomes and even other perfume raw material (perfume oils), as well as natural oils, including body and/or other soils.

III. Fiber-Assisted Delivery (FAD): The choice or use of an area may serve to improve the delivery of the organoleptic compounds of Formula I, stereoisomers thereof, and additional perfume materials. In fact, the area itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be pre-loaded with a perfume, and then added to a product that may or may not contain free perfume and/or one or more perfume delivery technologies.

IV. Amine Assisted Delivery (AAD): The amine-assisted delivery technology approach utilizes materials that contain an amine group to increase deposition or modify release of the organoleptic compounds of Formula I, stereoisomers thereof, and additional perfume materials during product use. There is no requirement in this approach to pre-complex or pre-react the perfume raw material(s) and the amine prior to addition to the product. Amine-containing AAD materials suitable for use herein may be non-aromatic, for example, polyalkylimine, such as polyethyleneimine (PEI), or polyvinylamine (PVAm); or aromatic, for example, anthranilates. Such materials may also be polymeric or non-polymeric. Such materials contain at least one primary amine. A material that contains a heteroatom other than nitrogen, for example sulfur, phosphorus or selenium, may be used as an alternative to amine compounds. In yet another aspect, the aforementioned alternative organoleptic compounds can be used in combination with amine compounds. In yet another aspect, a single molecule may comprise an amine moiety and one or more of the alternative heteroatom moieties, for example, thiols, phosphines and selenols.

V. Cyclodextrin Delivery System (CD): This technology approach uses a cyclic oligosaccharide or cyclodextrin to improve the delivery of the organoleptic compounds of Formula I, stereoisomers thereof, and additional perfume materials. Typically, the organoleptic compounds of Formula I, stereoisomers thereof, and/or additional perfume materials form a complex with cyclodextrin (CD) complex. Such complexes may be preformed, formed in-situ, or formed on or in the area.

VI. Starch Encapsulated Accord (SEA): SEA's are starch encapsulated perfume materials. Suitable starches include modified starches such as hydrolyzed starch, acid thinned starch, starch having hydrophobic groups, such as starch esters of long chain hydrocarbons (C5 or greater), starch acetates, starch octenyl succinate and mixtures thereof. Starch esters, such as starch octenyl succinates, are employed. Suitable perfumes for encapsulation include the HIA perfumes, including those having a boiling point determined at the normal standard pressure of about 760 mmHg of 275° C. or lower, an octanol/water partition coefficient P of about 2000 or higher and an odor detection threshold of less than or equal 50 parts per billion (ppb). The perfume may have log P of 2 or higher.

VII. Inorganic Carrier Delivery System (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry area. Another example of a suitable inorganic carrier includes inorganic tubules, where the perfume or other active material is contained within the lumen of the nano- or micro-tubules. Monomeric and/or polymeric materials, including starch encapsulation, may be used to coat, plug, cap, or otherwise encapsulate the PLZ.

VIII. Pro-Perfume (PP): This technology refers to perfume technologies that result from the reaction of the organoleptic compounds of Formula I, stereoisomers thereof, and additional perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Non-limiting examples of pro-perfumes include Michael adducts (e.g., beta-amino ketones), aromatic or non-aromatic imines (Schiffs Bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester. Silicone compounds, including aminosilicones, may be suitable and even preferred molecules for forming pro-perfume materials with PRMs; thus, the pro-perfume may be a silicone-based pro-perfume, preferably an aminosilicone-based pro-perfume. The PRMs may covalently bond with the silicone compound, for example by preferably forming an imine bond with a primary amine group of an aminosilicone, in one or more terminal or non-terminal, including pendant, positions of a silicone backbone. Silicones may be particularly preferred as pro-perfume carriers in that they may facilitate improved deposition of the PRM fragments onto a target surface, such as a fabric, prior to the release of the PRM. Such silicone-based delivery technologies are further disclosed in US Patent Application 2016/0137674A1 (assigned to The Procter & Gamble Company), incorporated herein by reference.

a.) Amine Reaction Product (ARP): For purposes of the present application, ARP is a subclass or species of PP. One may also use "reactive" polymeric amines in which the amine functionality is pre-reacted with one or more PRMs, typically PRMs that contain a ketone moiety and/or an aldehyde moiety, to form the ARP. Typically, the reactive amines are primary and/or secondary amines, and may be part of a polymer or a monomer (non-polymer). Such ARPs may also be mixed with additional PRMs to provide benefits of polymer-assisted delivery and/or amine-assisted delivery. Non-limiting examples of polymeric amines include polymers based on polyalkylimines, such as polyethyleneimine (PEI), or polyvinylamine (PVAm). Non-limiting examples of monomeric (non-polymeric) amines include hydroxyl amines, such as 2-aminoethanol and its alkyl substituted derivatives, and aromatic amines such as anthranilates. The ARPs may be premixed with perfume or added separately in leave-on or rinse-off applications. A material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols.

Methods of Use

Some of the consumer products disclosed herein can be used to clean or treat an area, such as a surface or fabric. In one example, at least a portion of the area is contacted with a consumer product, in neat form or diluted in a liquor, for example, a wash liquor and then the area may be optionally washed and/or rinsed. In one aspect, an area is optionally washed and/or rinsed, contacted with a the consumer product and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the area comprises a fabric, the water to fabric ratio is typically from about 1:1 to about 30:1.

The consumer product may also be sprayed onto the area to be treated. In some uses, after spraying, the consumer product may be wiped with a cleaning implement such as a sponge, cloth, towel, or substrate, for example. In some uses, after the area is sprayed with the consumer product, the area may be rinsed with water.

EXAMPLES

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, mmol is understood to be millimole, psig is understood to be pound-force per square inch gauge, and mmHg be millimeters (mm) of mercury (Hg). IFF as used in the examples is understood to mean International Flavors & Fragrances Inc., New York, N.Y., USA.

Example 1

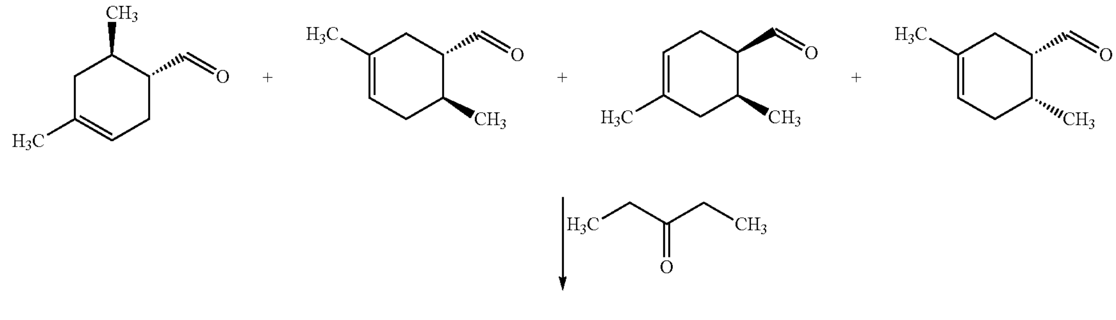

-continued

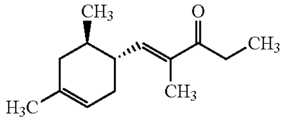
+
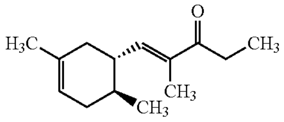
+
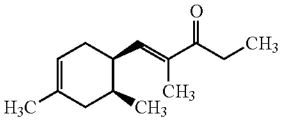
+
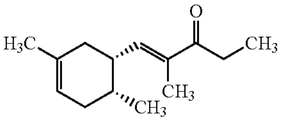

Sturcture 1 Sturcture 2 Sturcture 3 Sturcture 4

Preparation of (E)-1-((1R,6R)-4,6-Dimethylcyclohex-3-en-1-yl)-2-methylpent-1-en-3-one (Structure 1), (E)-1-((1S,6S)-3,6-Dimethylcyclohex-3-en-1-yl)-2-methylpent-1-en-3-one (Structure 2), (E)-1-((1R,6S)-4,6-Dimethylcyclohex-3-en-1-yl)-2-methylpent-1-en-3-one (Structure 3), and (E)-1-((1S,6R)-3,6-Dimethylcyclohex-3-en-1-yl)-2-methylpent-1-en-3-one (Structure 4)

Potassium hydroxide (KOH) (32.5 g, 0.58 mol) was dissolved in methanol ($CH_3OH$) (800 mL). A slight exotherm was observed. The reaction mixture was cooled to room temperature. 3-Pentanone ($(CH_3CH_2)_2CO$) (299 g, 3.5 mol) was slowly added to the mixture while the temperature was maintained at 20-25° C. An isomeric mixture of (6R)-4,6-dimethylcyclohex-3-ene-1-carbaldehyde, (1S,6S)-3,6-dimethylcyclohex-3-ene-1-carbaldehyde, (1R,6S)-4,6-dimethylcyclohex-3-ene-1-carbaldehyde and (1S,6R)-3,6-dimethylcyclohex-3-ene-1-carbaldehyde (400 g, 2.9 mol) (commercially available at IFF) was fed into the reaction mixture over 5-6 hours while the reaction mixture exothermed to 30-35° C. After the feeding was complete the reaction mixture was heated to and then maintained at 50-55° C. for 3-4 hrs. The reaction mixture was cooled to room temperature, quenched with glacial acetic acid ($CH_3COOH$) (30 g, 0.5 mol), and then heated to 80° C. to distill MeOH. The reaction mixture was subsequently washed with brine (500 mL). The aqueous layer was removed and the organic layer was distilled to afford the mixture of (E)-1-((1R,6R)-4,6-dimethylcyclohex-3-en-1-yl)-2-methylpent-1-en-3-one, (E)-1-((1S,6S)-3,6-dimethylcyclohex-3-en-1-yl)-2-methylpent-1-en-3-one, (E)-1-((1R,6S)-4,6-dimethylcyclohex-3-en-1-yl)-2-methylpent-1-en-3-one and (E)-1-((1S,6R)-3,6-dimethylcyclohex-3-en-1-yl)-2-methylpent-1-en-3-one (396 g) with a weight ratio of about 13:21:26:37 and having a with a boiling point of 122° C. at a pressure of 5 mmHg.

$^1H$ NMR (500 MHz, $CDCl_3$) δ: 6.39-6.58 (m, 1H), 5.31-5.37 (m, 1H), 2.24-2.78 (m, 1H), 2.64 (m, 2H), 1.60-2.20 (m, 4H), 1.95 (m, 1H), 1.77 (m, 3H), 1.65 (m, 3H), 1.07 (m, 3H), 0.84 (m, 3H)

The mixture of Structures 1-4 was described as having fresh, crispy, slight green, resinous, coniferous, floral, ionone-like, ambery and woody notes. Such desirable notes were also diffusive and blooming.

Example 2

Structure 9

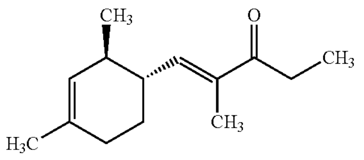

-continued

Structure 10

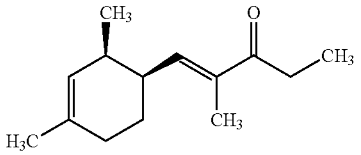

Preparation of (E)-1-((1R,2S)-2,4-Dimethylcyclohex-3-en-1-yl)-2-methylpent-1-en-3-one (Structure 9) and (E)-1-((1S,2S)-2,4-Dimethylcyclohex-3-en-1-yl)-2-methylpent-1-en-3-one (Structure 10)

The mixture of (E)-1-((1R,2S)-2,4-dimethylcyclohex-3-en-1-yl)-2-methylpent-1-en-3-one and (E)-1-((1S,2S)-2,4-dimethylcyclohex-3-en-1-yl)-2-methylpent-1-en-3-one with a weight ratio of about 69:28 was similarly prepared as above in EXAMPLE I from an isomeric mixture of (1R,2R)-2,4-dimethylcyclohex-3-ene-1-carbaldehyde and (1S,2R)-2,4-dimethylcyclohex-3-ene-1-carbaldehyde (commercially available at IFF).

(E)-1-((1R,2S)-2,4-Dimethylcyclohex-3-en-1-yl)-2-methylpent-1-en-3-one had the following NMR spectral characteristics:

$^1H$ NMR (400 MHz, $CDCl_3$) δ: 6.44 (dd, J=9.7, 1.3 Hz, 1H), 5.18-5.25 (m, 1H), 2.68 (q, J=7.4 Hz, 2H), 2.11-2.23 (m, 1H), 1.85-2.10 (m, 3H), 1.79 (d, J=1.4 Hz, 3H), 1.63-1.71 (m, 1H), 1.67 (s, 3H), 1.41-1.55 (m, 1H), 1.08 (t, J=7.4 Hz, 3H), 0.88 (d, J=6.8 Hz, 3H)

(E)-1-((1S,2S)-2,4-Dimethylcyclohex-3-en-1-yl)-2-methylpent-1-en-3-one had the following NMR spectral characteristics:

$^1H$ NMR (400 MHz, $CDCl_3$) δ: 6.60 (dd, J=9.7, 1.3 Hz, 1H), 5.25-5.29 (m, 1H), 2.70-2.80 (m, 1H), 2.66 (q, J=7.4 Hz, 2H), 2.32-2.42 (m, 1H), 1.85-2.10 (m, 2H), 1.80 (d, J=1.4 Hz, 3H), 1.63-1.71 (m, 2H), 1.67 (s, 3H), 1.07 (t, J=7.4 Hz, 3H), 0.87 (d, J=6.8 Hz, 3H)

The mixture of Structures 9 and 10 was described as having green, floral and woody notes.

In comparison of the two mixtures obtained from EXAMPLE I and EXAMPLE II, respectively, the mixture of Structures 1-4 exhibited significantly stronger, longer lasting and more complex notes. In contrast, the mixture of Structures 9 and 10 appeared weak, thin, less natural and harsh. The resinous and coniferous notes that were present in the Structures 1-4 mixture were also missing in the Structures 9 and 10 mixture.

Example 3

The mixture of (E)-1-((1R,6R)-4,6-dimethylcyclohex-3-en-1-yl)-2-methylpent-1-en-3-one, (E)-1-((1S,6S)-3,6-dimethylcyclohex-3-en-1-yl)-2-methylpent-1-en-3-one, (E)-1-((1R,6S)-4,6-dimethylcyclohex-3-en-1-yl)-2-methylpent-1-en-3-one and (E)-1-((1S,6R)-3,6-dimethylcyclohex-3-en-1-yl)-2-methylpent-1-en-3-one (25.0 g, 121 mmol) is dissolved in tetrahydrofuran (250 ml, 0.5M). The mixture is cooled to 0° C. and lithium aluminum hydride (2.3 g, 60.5 mmol) is added in small portions. The mixture is then allowed to warm up to room temperature. Stirring was continued for 50 minutes at this temperature to reach full conversion of the starting material.

The mixture is cooled to 0° C. Water (2.3 ml), aqueous sodium hydroxide (15%)(2.3 ml) and water (4.6 ml) are added to the mixture consecutively and the mixture is stirred at room temperature overnight. The mixture is filtered over a layer of celite, the filter cake is washed with tetrahydrofuran (50 ml). The filtrate is evaporated under reduced pressure and dried under high vacuum to yield 20 g of product. (79% yield)

Example 4: Preformed Amine Reaction Product

The following ingredients are weighted off in a glass vial:

1. 50% of a perfume composition comprising one or more organoleptic compounds of Structures 1, 2, 3, 4, or isomers thereof;
2. 50% of Lupasol WF (CAS #09002-98-6) from BASF, is put at 60° C. in warm water bath for 1 hour before use.

Mixing of the two ingredients is done by using the Ultra-Turrax T25 Basic equipment (from IKA) during 5 minutes. When the mixing is finished the sample is put in a warm water bath at 60° C. for ±12 hours. A homogenous, viscous material is obtained.

In the same way as described above different ratios between the components can be used:

| Weight % | | | | | |
|---|---|---|---|---|---|
| Perfume Composition | 40 | 50 | 60 | 70 | 80 |
| Lupasol WF | 60 | 50 | 40 | 30 | 20 |

Example 5: 84 wt % Core/16 wt % Wall Melamine Formaldehyde (MF) Capsule PAD Reservoir System 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil comprising Structures 1, 2, 3, 4, or isomers thereof of Formula I is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stirring to complete the encapsulation process. 23 grams of acetoacetamide (Sigma-Aldrich, Saint Louis, Mo., U.S.A.) is added to the suspension. An average capsule size of 30 um is obtained as analyzed by a Model 780 Accusizer.

Example 6: Polyacrylate Based Capsule PAD Reservoir System

Suitable perfume capsules can be purchased from Encapsys, (825 East Wisconsin Ave, Appleton, Wis. 54911), and are made as follows: a first oil phase, consisting of 37.5 g perfume, 0.2 g tert-butylamino ethyl methoacrylate, and 0.2 g beta hydroxyethyl acrylate is mixed for about 1 hour before the addition of 18 g CN975 (Sartomer, Exter, Pa.). The solution is allowed to mix until needed later in the process.

A second oil phase consisting of 65 g of the organoleptic compound of Formula I and stereoisomers thereof, 84 g isopropyl myristate, 1 g 2,2'-azobis(2-methylbutyronitrile), and 0.8 g 4,4'-azobis[4-cyanovaleric acid] is added to a jacketed steel reactor. The reactor is held at 35° C. and the oil solution in mixed at 500 rpm's with a 2" flat blade mixer. A nitrogen blanket is applied to the reactor at a rate of 300 cc/min. The solution is heated to 70° C. in 45 minutes and held at 70° C. for 45 minutes, before cooling to 50° C. in 75 minutes. At 50° C., the first oil phase is added and the combined oils are mixed for another 10 minutes at 50° C.

A water phase, containing 85 g Celvol 540 PVA (Sekisui Specialty Chemicals, Dallas, Tex.) at 5% solids, 268 g water, 1.2 g 4,4'-azobis[4-cyanovaleric acid], and 1.1 g 21.5% NaOH, is prepared and mixed until the 4,4'-AZOBIS[4-CYANOVALERIC ACID] dissolves. The water phase pH for this batch was 4.90.

Once the oil phase temperature has decreased to 50° C., mixing is stopped and the water phase is added to the mixed oils. High shear agitation is applied to produce an emulsion with the desired size characteristics (1900 rpm's for 60 minutes.)

The temperature was increased to 75° C. in 30 minutes, held at 75° C. for 4 hours, increased to 95° C. in 30 minutes, and held at 95° C. for 6 hours. The batch was allowed to cool to room temperature.

Example 7: Process of Making a Polymer Assisted Delivery (PAD) Matrix System

A mixture comprising 50% of a perfume composition comprising one or more of Structures 1, 2, 3, 4, or isomers thereof of Formula 1, 40% of carboxyl-terminated Hycar®1300X18 (CAS #0068891-50-9) from Noveon, (put at 60° C. in warm water bath for 1 hour before mixing) and 10% of Lupasol® WF(CAS #09002-98-6) from BASF (put at 60° C. in warm water bath for 1 hour before mixing). Mixing is achieved by mixing for five minutes using a Ultra-Turrax T25 Basic equipment (from IKA). After mixing, the mixture is put in a warm water bath at 60° C. for ±12 hours. A homogenous, viscous and sticky material is obtained.

In the same way as described above different ratios between the components can be used:

| Weight % | | | | | |
|---|---|---|---|---|---|
| Perfume Composition | 40 | 50 | 60 | 70 | 80 |
| Lupasol ® WF | 12 | 10 | 8 | 6 | 4 |
| Hycar ® CTBN1300X18 | 48 | 40 | 32 | 24 | 16 |

| | Weight % | | | | | | | |
|---|---|---|---|---|---|---|---|---|
| Perfume composition | 50 | 50 | 50 | 50 | 50 | 50 | 50 | 50 |
| Lupasol ® WF | 2.5 | 5 | 7.5 | 10 | 12.5 | 15 | 17.5 | 20 |
| Hycar ® CTBN 1300X18 | 47.5 | 45 | 42.5 | 40 | 37.5 | 35 | 32.5 | 30 |

Example 8: Product Formulation

Non-limiting examples of product formulations containing PRMs disclosed in the present specification perfume and amines summarized in the following table.

| | EXAMPLES | | | | | | | | | |
|---|---|---|---|---|---|---|---|---|---|---|
| (% wt) | XI | XII | XIII | XIV | XV | XVI | XVII | XVIII | XIX | XX |
| FSA [a] | 14 | 16.47 | 14 | 12 | 12 | 16.47 | — | — | 5 | 5 |
| FSA [b] | | | | | — | | 3.00 | — | — | — |
| FSA [c] | | | | | — | | — | 6.5 | — | — |
| Ethanol | 2.18 | 2.57 | 2.18 | 1.95 | 1.95 | 2.57 | — | — | 0.81 | 0.81 |
| Isopropyl Alcohol | — | — | — | — | — | — | 0.33 | 1.22 | — | — |
| Starch [d] | 1.25 | 1.47 | 2.00 | 1.25 | — | 2.30 | 0.5 | 0.70 | 0.71 | 0.42 |
| Amine* | 0.6 | 0.75 | 0.6 | 0.75 | 0.37 | 0.60 | 0.37 | 0.6 | 0.37 | 0.37 |
| Perfume X[e] | 0.40 | 0.13 | 0.065 | 0.25 | 0.03 | 0.030 | 0.030 | 0.065 | 0.03 | 0.03 |
| Phase Stabilizing Polymer [f] | 0.21 | 0.25 | 0.21 | 0.21 | 0.14 | — | — | 0.14 | — | — |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | — |
| DTPA [h] | 0.017 | 0.017 | 0.017 | 0.017 | 0.007 | 0.007 | 0.20 | — | 0.002 | 0.002 |
| Preservative (ppm) [i, j] | 5 | 5 | 5 | 5 | 5 | 5 | — | 250 [j] | 5 | 5 |
| Antifoam[k] | 0.015 | 0.018 | 0.015 | 0.015 | 0.015 | 0.015 | — | — | 0.015 | 0.015 |
| Dye (ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Structurant[l] | 0.01 | 0.01 | 0.01 | 0.01 | 0.01 | 0.01 | 0.01 | 0.01 | 0.01 | 0.01 |
| Additional Neat Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a] N,N-di(tallowoyloxyethyl)-N,N-dimethylammonium chloride.

[b] Methyl bis(tallow amidoethyl)2-hydroxyethyl ammonium methyl sulfate.

[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.

[d] Cationic high amylose maize starch available from National Starch under the trade name CATO ®.

[e]Perfume comprising one or more of Structures 1, 2, 3, 4, and isomers thereof of Formula I above.

[f] Copolymer of ethylene oxide and terephthalate having the formula described in U.S. Pat. No. 5,574,179 at col. 15, lines 1-5, wherein each X is methyl, each n is 40, u is 4, each R1 is essentially 1,4-phenylene moieties, each R2 is essentially ethylene, 1,2-propylene moieties, or mixtures thereof.

[g] SE39 from Wacker

[h] Diethylenetriaminepentaacetic acid.

[i] KATHON ® CG available from Rohm and Haas Co. "PPM" is "parts per million."

[j] Gluteraldehyde

[k]Silicone antifoam agent available from Dow Corning Corp. under the trade name DC2310.

[l]Hydrophobically-modified ethoxylated urethane available from Rohm and Haas under the tradename Aculan 44.

*One or more materials comprising an amine moiety as disclosed in the present specification.

† balance

Example 9: Dry Laundry Formulations

| | % w/w granular laundry detergent composition | | | | | | |
|---|---|---|---|---|---|---|---|
| Component | A | B | C | D | E | F | G |
| Brightener | 0.1 | 0.1 | 0.1 | 0.2 | 0.1 | 0.2 | 0.1 |
| Soap | 0.6 | 0.6 | 0.6 | 0.6 | 0.6 | 0.6 | 0.6 |

-continued

| | % w/w granular laundry detergent composition | | | | | | |
|---|---|---|---|---|---|---|---|
| Component | A | B | C | D | E | F | G |
| Ethylenediamine disuccinic acid | 0.1 | 0.1 | 0.1 | 0.1 | 0.1 | 0.1 | 0.1 |
| Acrylate/maleate copolymer | 1.5 | 1.5 | 1.5 | 1.5 | 1.5 | 1.5 | 1.5 |
| Hydroxyethane di(methylene phosphonic acid) | 0.4 | 0.4 | 0.4 | 0.4 | 0.4 | 0.4 | 0.4 |
| Mono-$C_{12-14}$ alkyl, di-methyl, mono-hydroyethyl quaternary ammonium chloride | 0.5 | 0.5 | 0.5 | 0.5 | 0.5 | 0.5 | 0.5 |
| Linear alkyl benzene | 0.1 | 0.1 | 0.2 | 0.1 | 0.1 | 0.2 | 0.1 |
| Linear alkyl benzene sulphonate | 10.3 | 10.1 | 19.9 | 14.7 | 10.3 | 17 | 10.5 |
| Magnesium sulphate | 0.4 | 0.4 | 0.4 | 0.4 | 0.4 | 0.4 | 0.4 |
| Sodium carbonate | 19.5 | 19.2 | 10.1 | 18.5 | 29.9 | 10.1 | 16.8 |
| Sodium sulphate | 29.6 | 29.8 | 38.8 | 15.1 | 24.4 | 19.7 | 19.1 |
| Sodium Chloride | 0.1 | 0.1 | 0.1 | 0.1 | 0.1 | 0.1 | 0.1 |
| Zeolite | 9.6 | 9.4 | 8.1 | 18 | 10 | 13.2 | 17.3 |
| Photobleach particle | 0.1 | 0.1 | 0.2 | 0.1 | 0.2 | 0.1 | 0.2 |
| Blue and red carbonate speckles | 1.8 | 1.8 | 1.8 | 1.8 | 1.8 | 1.8 | 1.8 |
| Ethoxylated Alcohol AE7 | 1 | 1 | 1 | 1 | 1 | 1 | 1 |
| Tetraacetyl ethylene diamine agglomerate (92 wt % active) | 0.9 | 0.9 | 0.9 | 0.9 | 0.9 | 0.9 | 0.9 |
| Citric acid | 1.4 | 1.4 | 1.4 | 1.4 | 1.4 | 1.4 | 1.4 |
| PDMS/clay agglomerates (9.5% wt % active PDMS) | 10.5 | 10.3 | 5 | 15 | 5.1 | 7.3 | 10.2 |
| Polyethylene oxide | 0.2 | 0.2 | 0.2 | 0.2 | 0.2 | 0.2 | 0.2 |
| Enzymes e.g. Protease (84 mg/g active), Amylase (22 mg/g active) | 0.2 | 0.3 | 0.2 | 0.1 | 0.2 | 0.1 | 0.2 |
| Suds suppressor agglomerate (12.4 wt % active) | 0.2 | 0.2 | 0.2 | 0.2 | 0.2 | 0.2 | 0.2 |
| Sodium percarbonate (having from 12% to 15% active AvOx) | 7.2 | 7.1 | 4.9 | 5.4 | 6.9 | 19.3 | 13.1 |
| Additional Neat Perfume** | 0.5 | 0.5 | 0.5 | 0.5 | 0.5 | 0.5 | 0.5 |
| Amine* | 0.1 | 0.5 | 0.0 | 0.01 | 0.02 | 0.00 | 0.07 |
| Perfume Delivery System As Disclosed In The Present Specification Including Examples 3-5 | 0.05 | 0.0 | 0.1 | 0.0 | 0.2 | 0.4 | 0.0 |
| Perfume comprising one or more of Structures 1, 2, 3, 4, and isomers there of Formula I above | 0.3 | 0.4 | 0.01 | 0.02 | 0.04 | 0.1 | 0.1 |
| Water | 1.4 | 1.4 | 1.4 | 1.4 | 1.4 | 1.4 | 1.4 |
| Misc | 0.1 | 0.1 | 0.1 | 0.1 | 0.1 | 0.1 | 0.1 |
| Total Parts | 100 | 100 | 100 | 100 | 100 | 100 | 100 |

*One or more materials comprising an amine moiety as disclosed in the present specification.

**Optional

Example 10: Liquid Laundry Formulations (HDLs)

| Ingredient | HDL 1 | HDL 2 | HDL3 | HDL4 | HDL 5 | HDL 6 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |

-continued

| Ingredient | HDL 1 | HDL 2 | HDL3 | HDL4 | HDL 5 | HDL 6 |
|---|---|---|---|---|---|---|
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Additional Neat Perfume** | 0.7 | 0.5 | 0.8 | 0.8 | 0.6 | 0.6 |
| Amine* | 0.01 | 0.10 | 0.0 | 0.10 | 0.20 | 0.05 |
| Perfume comprising one or more of Structures 1, 2, 3, 4, and isomers there of Formula I above | 0.02 | 0.15 | 0.0 | 0.2 | 0.3 | 0.1 |
| Perfume Delivery System As Disclosed In The Present Specification Including Examples 3-4 | 0.2 | 0.02 | 0.4 | 0.0 | 0.0 | 0.0 |
| Water | Balance | Balance | Balance | Balance | Balance | Balance |

*One or more materials comprising an amine moiety as disclosed in the present specification.
**Optional.

Example 11: Shampoo Formulations

| Ingredient | |
|---|---|
| Ammonium Laureth Sulfate ($AE_3S$) | 6.00 |
| Ammonium Lauryl Sulfate (ALS) | 10.00 |
| Laureth-4 Alcohol | 0.90 |
| Trihydroxystearin (7) | 0.10 |
| Perfume comprising one or more of Structures 1, 2, 3, 4, and isomers there of Formula I above | 0.60 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone (9, 10, 11) | 1.00 (9) |
| Water and Minors (QS to 100%) | Balance |

Example 12: Preparation of an Exemplary Silicone-Based Pro-Perfume Comprising an Organoleptic Compound According to the Present Disclosure To form a silicone-based pro-perfume, 50.0 g of an aminosilicone (KF-8003 silicone, available from Shin-Etsu Silicones; 0.0264 mol) and 5.45 g of an organoleptic compound according to the present disclosure (0.0264 mol) are weighed into a 250 mL three-neck flask containing a magnetic stir bar. The reaction mixture is stirred for 24 h at 80° C. under nitrogen sweep (to remove water). Formation of imine bond is analyzed using $^{13}C$-NMR.

The general reaction is represented according to the equation below, where R—$NH_2$ represents the starting aminosilicone. It is understood that the starting aminosilicone includes a plurality of —$NH_2$ moieties, and that the reaction provided below may occur at more than one —$NH_2$ moiety on the aminosilicone. This advantageously results in a plurality of organoleptic compounds being loaded onto the aminosilicone.

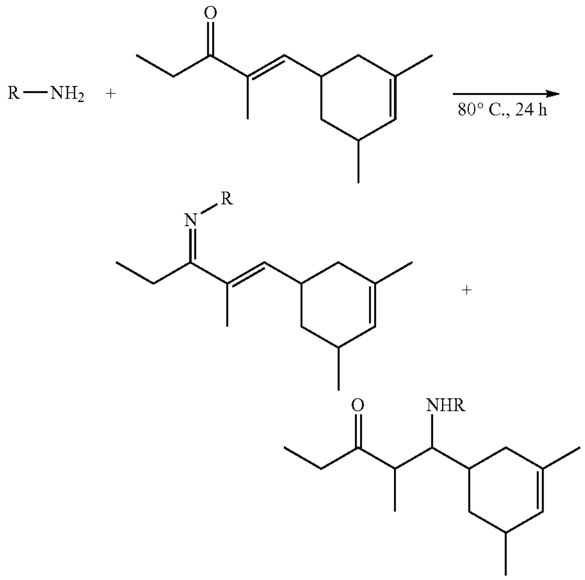

The pro-perfume reaction product may be suitable for formulating into a consumer product, such as a fabric care product (e.g., a liquid fabric enhancer).

It is further understood that different aminosilicones may be substituted for the exemplified KF-8003 aminosilicone, but that the reaction shown above may remain substantially the same.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product comprising an organoleptic compound selected from the group consisting of:

(E)-1-((1R,6R)-4,6-dimethylcyclohex-3-en-1-yl)-2-methylpent-1-en-3-one;

(E)-1-((1S,6S)-3,6-dimethylcyclohex-3-en-1-yl)-2-methylpent-1-en-3-one;

(E)-1-((1R,6S)-4,6-dimethylcyclohex-3-en-1-yl)-2-methylpent-1-en-3-one;

(E)-1-((1S,6R)-3,6-dimethylcyclohex-3-en-1-yl)-2-methylpent-1-en-3-one;

(E)-1-((1R,6R)-4,6-dimethylcyclohex-3-en-1-yl)-2-methylpent-1-en-3-ol;

(E)-1-((1S,6S)-3,6-dimethylcyclohex-3-en-1-yl)-2-methylpent-1-en-3-ol;

(E)-1-((1R,6S)-4,6-dimethylcyclohex-3-en-1-yl)-2-methylpent-1-en-3-ol;

(E)-1-((1S,6R)-3,6-dimethylcyclohex-3-en-1-yl)-2-methylpent-1-en-3-ol; and a mixture thereof.

2. The consumer product according to claim 1, wherein the organoleptic compound is the mixture of (E)-1-((1R,6R)-4,6-dimethylcyclohex-3-en-1-yl)-2-methylpent-1-en-3-one, (E)-1-((1S,6S)-3,6-dimethylcyclohex-3-en-1-yl)-2-methylpent-1-en-3-one, (E)-1-((1R,6S)-4,6-dimethylcyclohex-3-en-1-yl)-2-methylpent-1-en-3-one and (E)-1-((1S,6R)-3,6-dimethylcyclohex-3-en-1-yl)-2-methylpent-1-en-3-one.

3. The consumer product according to claim 1, wherein the composition comprises, based on total composition weight, from about 0.0001% to about 25% of the organoleptic compound.

4. The consumer product according to claim 1, wherein the consumer product is a fabric and/or hard surface cleaning and/or treatment composition, said composition comprising, based on total composition weight, from about 0.00001% to about 25% of the organoleptic compound.

5. The consumer product according to claim 1, wherein the consumer product is a detergent, said detergent comprising, based on total detergent weight, from about 0.00001% to about 25% of the organoleptic compound.

6. The consumer product according to claim 1, wherein the consumer product is a highly compacted consumer product, said highly compacted consumer product comprising, based on total highly compacted consumer product weight, from about 0.00001% to about 25% of the organoleptic compound.

7. A method of treating an area with the consumer product of claim 1.

8. A perfume delivery system comprising an organoleptic compound selected from the group consisting of:

(E)-1-((1R,6R)-4,6-dimethylcyclohex-3-en-1-yl)-2-methylpent-1-en-3-one;

(E)-1-((1S,6S)-3,6-dimethylcyclohex-3-en-1-yl)-2-methylpent-1-en-3-one;

(E)-1-((1R,6S)-4,6-dimethylcyclohex-3-en-1-yl)-2-methylpent-1-en-3-one;

(E)-1-((1S,6R)-3,6-dimethylcyclohex-3-en-1-yl)-2-methylpent-1-en-3-one;

(E)-1-((1R,6R)-4,6-dimethylcyclohex-3-en-1-yl)-2-methylpent-1-en-3-ol;

(E)-1-((1S,6S)-3,6-dimethylcyclohex-3-en-1-yl)-2-methylpent-1-en-3-ol;

(E)-1-((1R,6S)-4,6-dimethylcyclohex-3-en-1-yl)-2-methylpent-1-en-3-ol;

(E)-1-((1S,6R)-3,6-dimethylcyclohex-3-en-1-yl)-2-methylpent-1-en-3-ol; and a mixture thereof.

9. The perfume delivery system of claim 8, wherein said perfume delivery system is selected from a polymer assisted delivery system; a molecule-assisted delivery system; a fiber-assisted delivery system; an amine assisted delivery system; a cyclodextrin delivery system; a starch encapsulated accord; an inorganic carrier delivery system; or a pro-perfume.

10. The perfume delivery system of claim 9, wherein the organoleptic compound is the mixture of (E)-1-((1R,6R)-4,6-dimethylcyclohex-3-en-1-yl)-2-methylpent-1-en-3-one, (E)-1-((1S,6S)-3,6-dimethylcyclohex-3-en-1-yl)-2-methylpent-1-en-3-one, (E)-1-((1R,6S)-4,6-dimethylcyclohex-3-en-1-yl)-2-methylpent-1-en-3-one and (E)-1-((1S,6R)-3,6-dimethylcyclohex-3-en-1-yl)-2-methylpent-1-en-3-one.

11. The perfume delivery system of claim 8 further comprising, based on total perfume delivery system weight, from about 0.1% to about 99% of the organoleptic compound.

12. The perfume delivery system according to claim 8, wherein the perfume delivery system is a capsule.

13. The perfume delivery system according to claim 8, wherein perfume delivery system is a starch encapsulated accord.

14. The perfume delivery system according to claim 8, wherein the perfume delivery system is a cyclodextrin delivery system comprising, based on total cyclodextrin delivery system weight, from 0.1% to about 99% of the organoleptic compound.

15. The perfume delivery system according to claim 8, wherein the perfume delivery system is a polymer assisted delivery matrix system comprising, based on total polymer assisted delivery matrix system weight, from 0.1% to about 99% of the organoleptic compound.

16. The perfume delivery system according to claim 8, wherein the perfume delivery system is an amine assisted delivery system comprising, based on total amine assisted delivery system weight, from 1% to about 99% of the organoleptic compound.

17. The perfume delivery system according to claim 8, wherein the perfume delivery system is a pro-perfume amine reaction product comprising, based on total pro-perfume amine reaction product weight, from 0.10% to about 99% of the organoleptic compound.

18. A method of treating an area with a consumer product comprising the perfume delivery system of claim 8.

* * * * *